(12) United States Patent
Brunner

(10) Patent No.: US 7,581,410 B2
(45) Date of Patent: Sep. 1, 2009

(54) LOW TEMPERATURE TESTING DEVICE FOR ELECTRONIC COMPONENTS

(75) Inventor: Franz Brunner, Rohrdorf (DE)

(73) Assignee: Multitest Elektronische Systeme GmbH, Rosenheim (DE)

( * ) Notice: Subject to any disclaimer, the term of this patent is extended or adjusted under 35 U.S.C. 154(b) by 520 days.

(21) Appl. No.: 11/183,974

(22) Filed: Jul. 19, 2005

(65) Prior Publication Data

US 2006/0037412 A1    Feb. 23, 2006

(30) Foreign Application Priority Data

Aug. 20, 2004  (DE) ........................ 10 2004 040 527

(51) Int. Cl.
  *F25D 23/12* (2006.01)
(52) U.S. Cl. ...................... 62/259.2; 62/50.2
(58) Field of Classification Search .................. 62/50.2, 62/259.2, 50.4; 73/865.6
  See application file for complete search history.

(56) References Cited

U.S. PATENT DOCUMENTS

| 4,787,752 A | 11/1988 | Fraser et al. |
| 5,084,671 A * | 1/1992 | Miyata et al. ............... 324/760 |
| 6,525,527 B1 | 2/2003 | Seong et al. |
| 6,711,961 B2 * | 3/2004 | Theriault et al. ........... 73/865.6 |

* cited by examiner

*Primary Examiner*—Melvin Jones
(74) *Attorney, Agent, or Firm*—Nixon & Vanderhye P.C.

(57) ABSTRACT

In a cold test device for electronic components, there are a cryogenic fluid supply line (5) for supply of a liquid cryogenic fluid, an evaporator (9), a cryogenic fluid line (11) for transporting the gaseous cryogenic fluid to the electronic component (3), in the cryogenic fluid line (11) which transports the gaseous cryogenic fluid there being a volumetric flow regulator (13, 13', 13") which stabilizes the pressure and the volumetric flow of cryogenic fluid.

12 Claims, 7 Drawing Sheets

Figure 1:
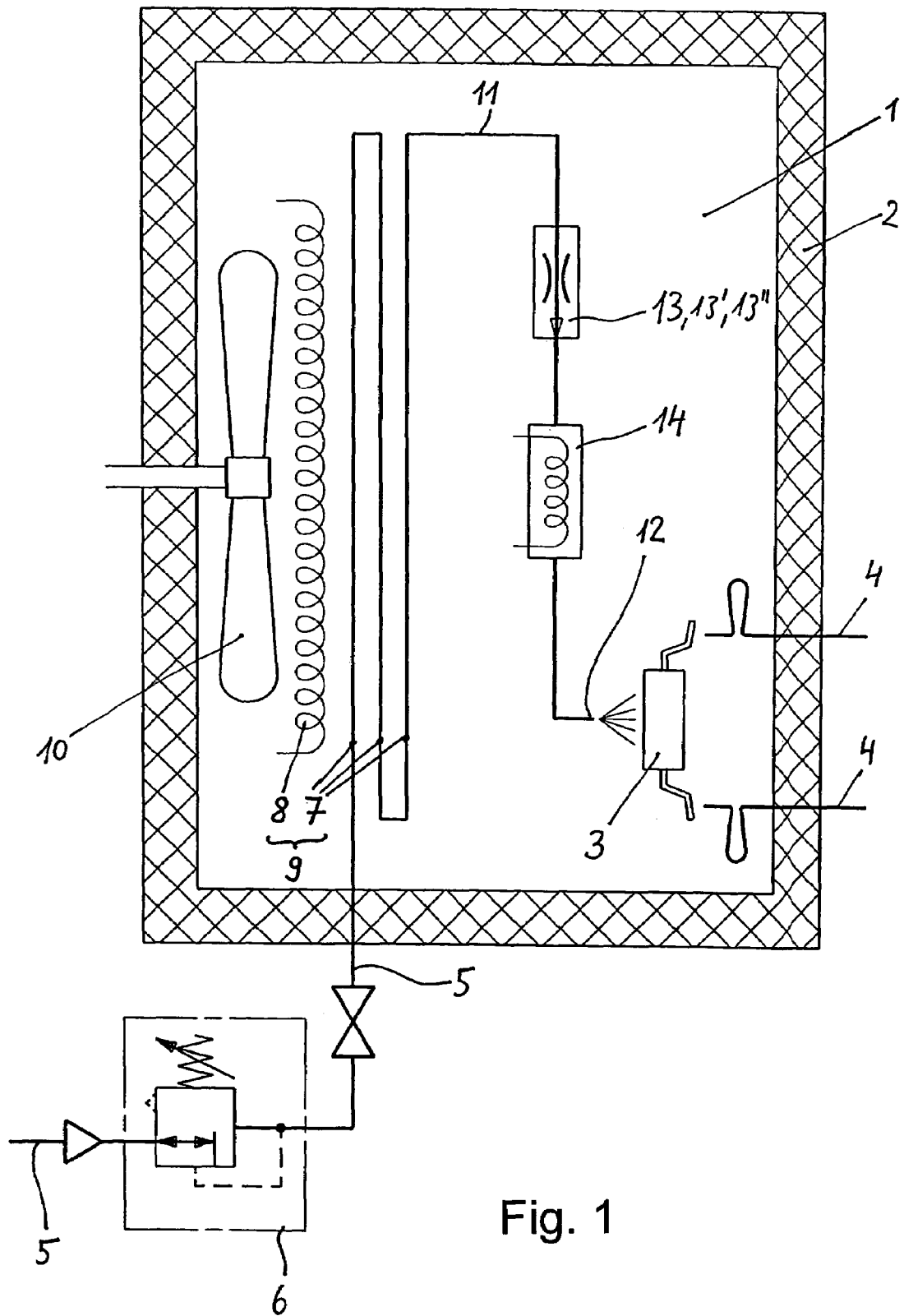

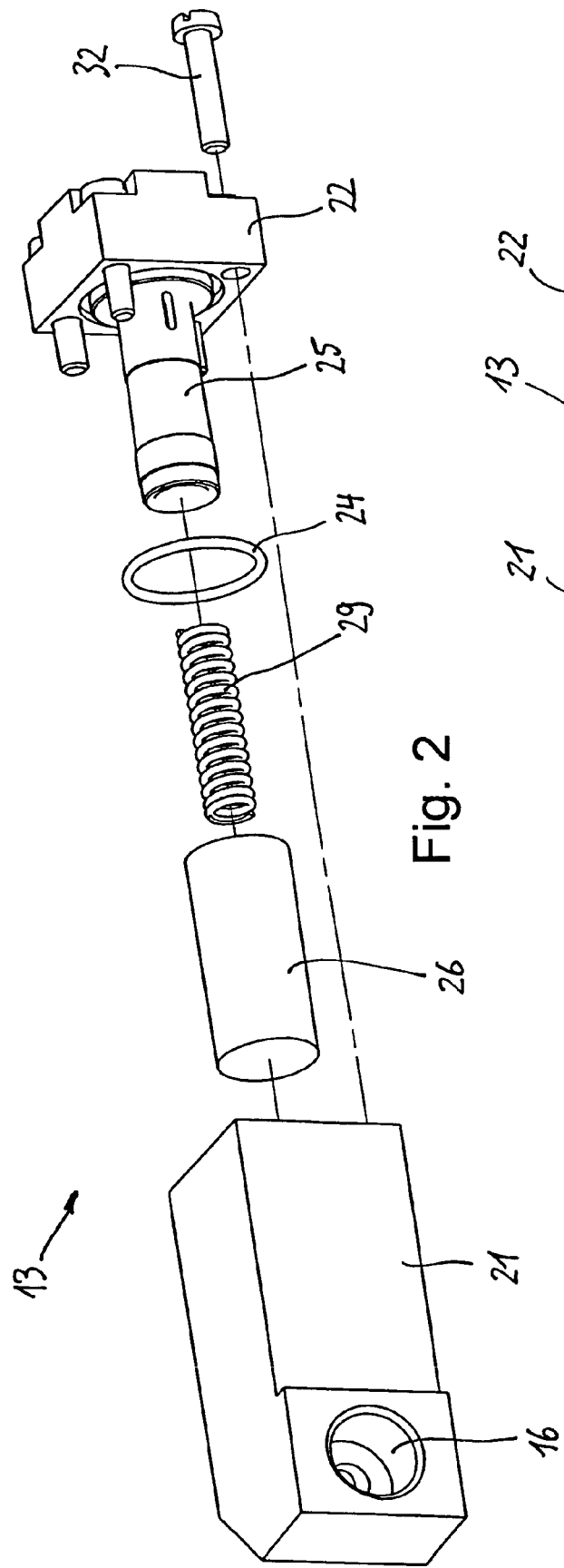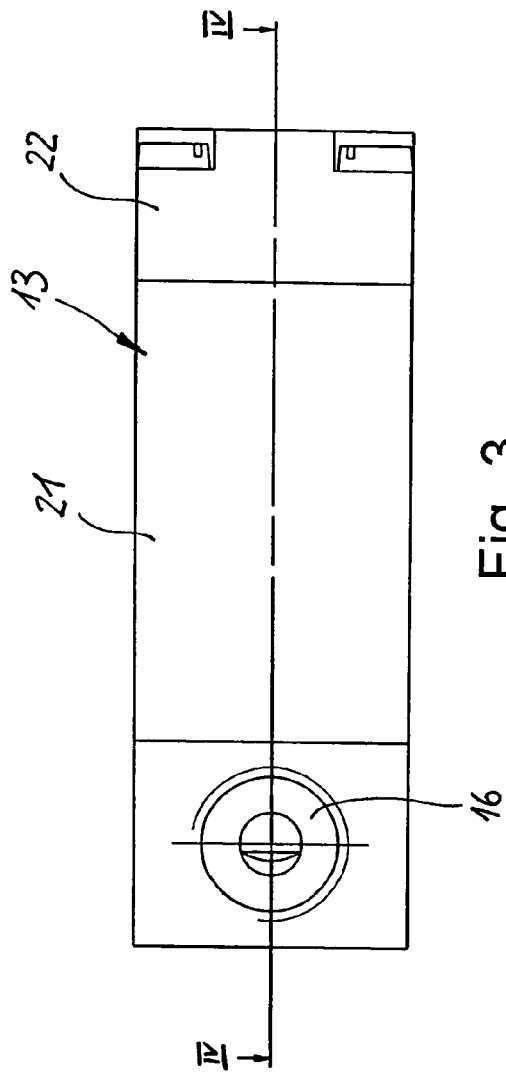
Fig. 2
Fig. 3

LOW TEMPERATURE TESTING DEVICE FOR ELECTRONIC COMPONENTS

The invention relates to a cold test device for electronic components as claimed in the preamble of claim 1.

Exposing electronic components, for example microchips with integrated circuits, to low temperatures of for example −60° C. in cold chambers in order to test the low temperature properties of electronic components is known. In doing so the electronic component is exposed to an incident flow of cold gaseous nitrogen in a cold chamber. To do this, first of all liquid nitrogen with a temperature of roughly −196° C. or lower is supplied to the cold chamber and evaporated by means of an evaporator. The nitrogen which now has a gaseous state is then routed to a heating device with which the gas is heated to such an extent that the desired temperature, for example −60° C., is reached at the outlet of the cryogenic fluid line. The heating device thus constitutes a part of a control means with which the temperature of the gas is set.

In this known process, the problem is that when the liquid nitrogen is evaporated in the evaporator, pressure and volumetric flow fluctuations form in the cryogenic fluid line, by which major temperature fluctuations which are outside of the tolerance range of for example 0.5° C. can occur at the outlet of the cryogenic fluid line. These pressure and volumetric flow fluctuations can be reduced if the cryogenic fluid line is lengthened. But in addition to an increased demand for space, this has the additional disadvantage that in the cryogenic fluid line thermal conduction processes can cause such a dramatic heating of the gaseous nitrogen that it is no longer possible to exactly set the temperature by means of the heating device. Therefore, fundamentally efforts are made to keep the cryogenic fluid line as short as possible so that the temperature of the gas upstream of the heating device is low enough below the theoretical temperature at the outlet of the cryogenic fluid line in order to be able to set the exact theoretical temperature by means of the heating device. But this leads to the aforementioned stability problems with respect to pressure, volumetric flow and temperature.

The object of the invention is to devise a cold test device of the initially mentioned type with which the desired theoretical temperature of the gaseous cryogenic fluid at the outlet of the cryogenic fluid line can be maintained especially exactly, even for short lengths of the cryogenic fluid line.

This object is achieved as claimed in the invention by the features of claim 1. Advantageous embodiments of the invention are described in the other claims.

In the cold test device as claimed in the invention, in the cryogenic fluid line which transports the gaseous cryogenic fluid there is a volumetric flow regulator which stabilizes the pressure and the volumetric flow of the cryogenic fluid.

The volumetric flow regulator offers the advantage that within the cryogenic fluid line only minor pipe vibrations of the gaseous cryogenic fluid occur. The pressure and volumetric flow in the cryogenic fluid line are thus at least roughly constant, by which the temperature stability of the gaseous cryogenic fluid is distinctly improved. In this way it is thus also possible to shorten the cryogenic fluid line between the evaporator and heating device if the temperature of the gaseous cryogenic fluid upstream of the heating device is to be reduced in order to increase the temperature difference between the temperature upstream of the heating means and the theoretical temperature at the outlet of the cryogenic fluid line and thus to obtain better temperature setting possibilities by the heating means. Furthermore the volumetric flow regulator as claimed in the invention offers the advantage that the entire system is also less susceptible to pressure fluctuations in the cryogenic fluid supply line at the inlet of the cold chamber. An additional pressure regulator at the inlet of the cold chamber is not necessary even at higher supply pressures.

The volumetric flow regulator which is advantageously provided between the evaporator and the heating means according to one advantageous embodiment has a housing with a cryogenic fluid inlet, a cryogenic fluid outlet and a spool chamber which is located between the cryogenic fluid inlet and cryogenic fluid outlet and in which a throttle slide valve can be moved by means of the inflowing gaseous cryogenic fluid against the pretensioning force of a spring, by which the volumetric flow flowing through the volumetric flow regulator can be varied. Such a volumetric flow regulator works automatically based solely on pressure fluctuations in the line system of the gaseous cryogenic fluid, without the need for additional sensors or electrical control means. It is a technically reliable engineering approach which can be produced relatively economically.

The invention is detailed below using drawings by way of example.

Figure 4:
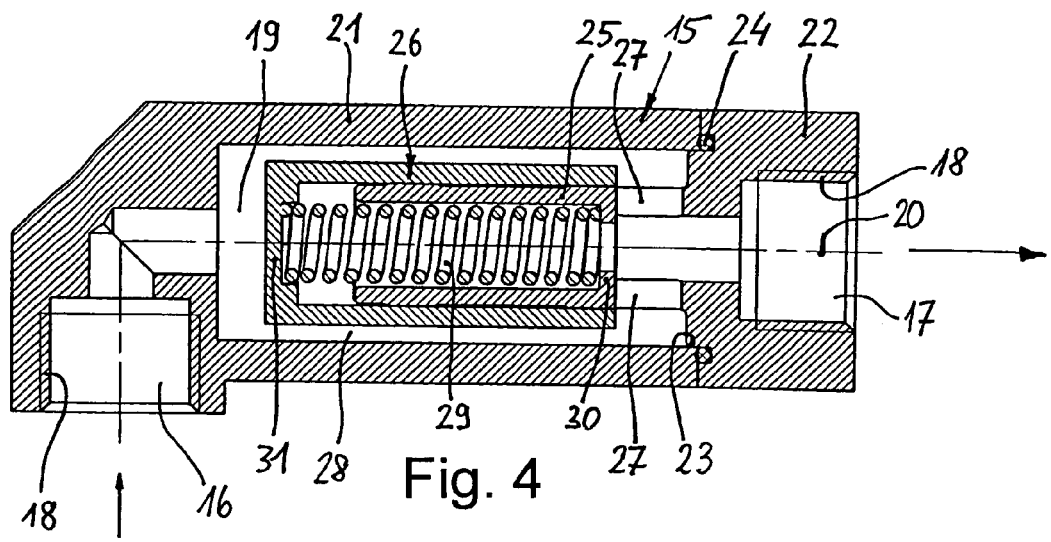
Figure 5:
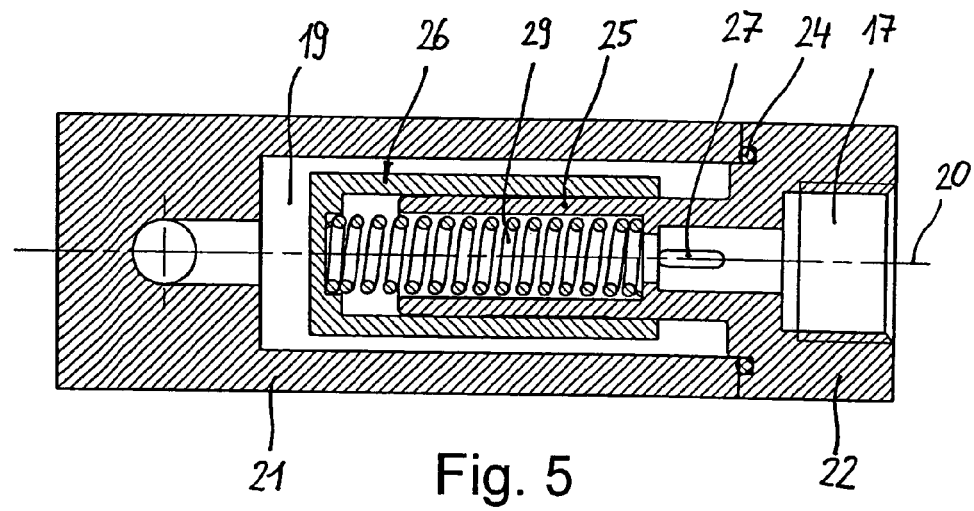
Figure 6:
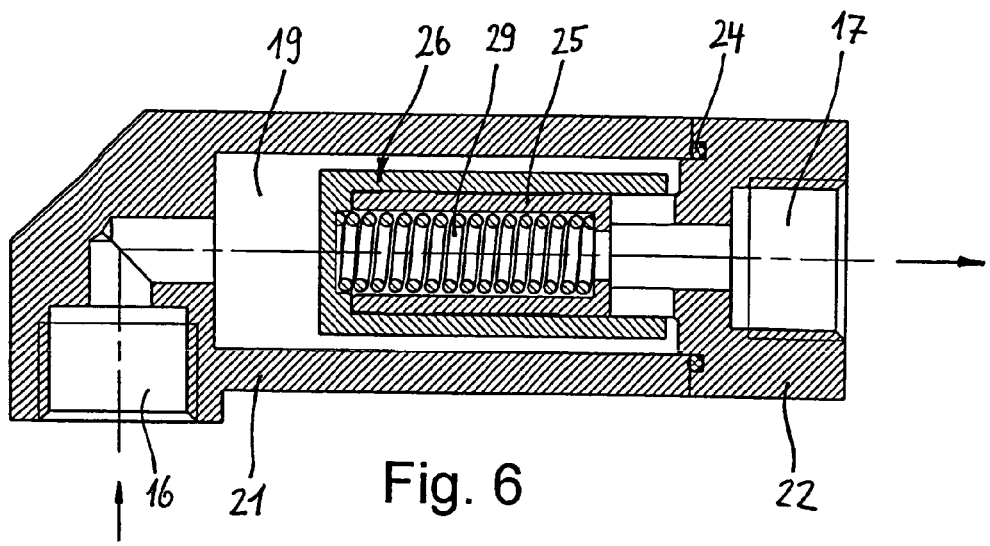
Figure 7:
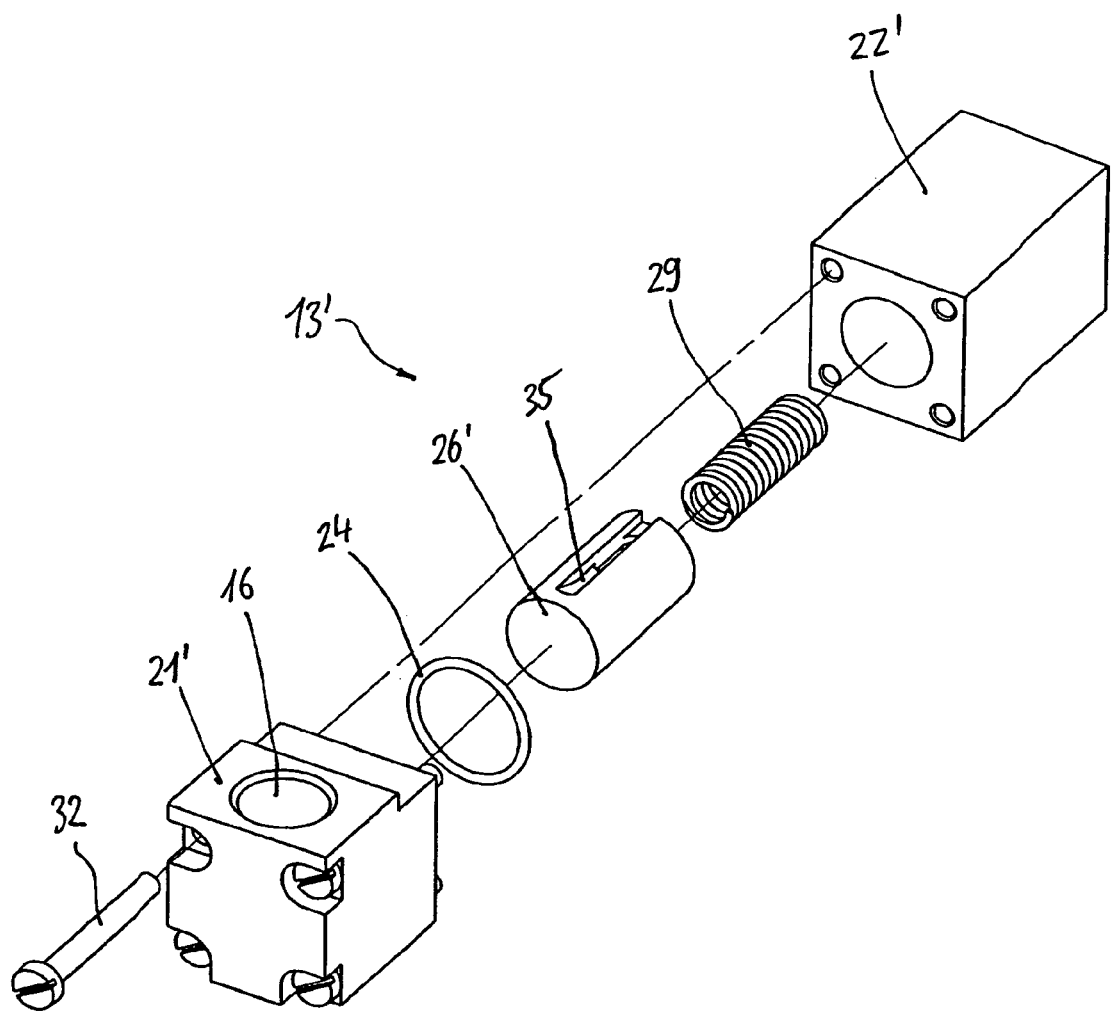
Figure 8:
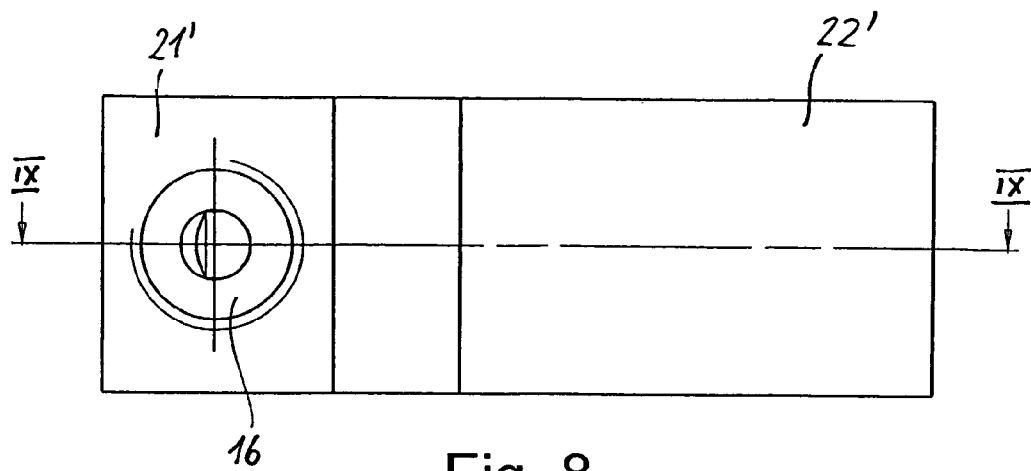
Figure 9:
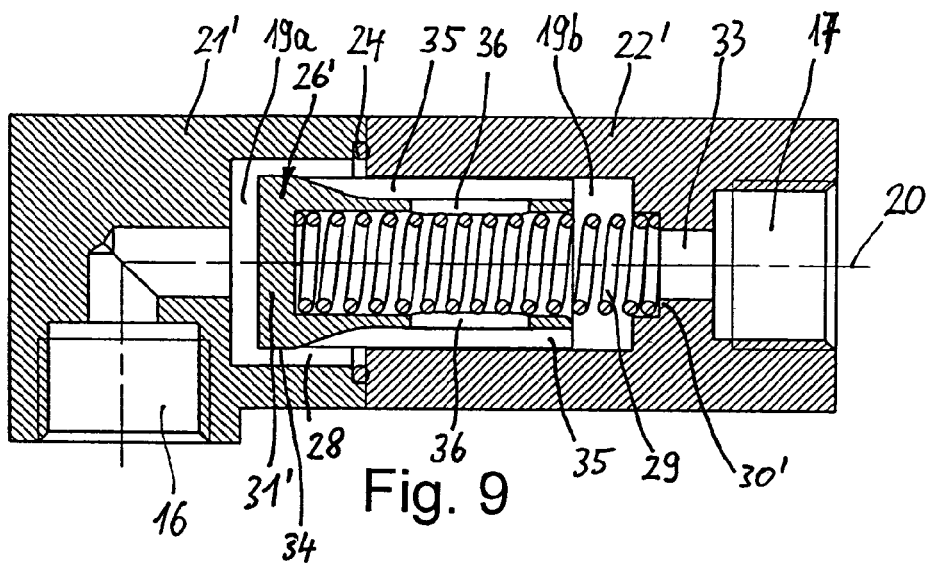
Figure 10:
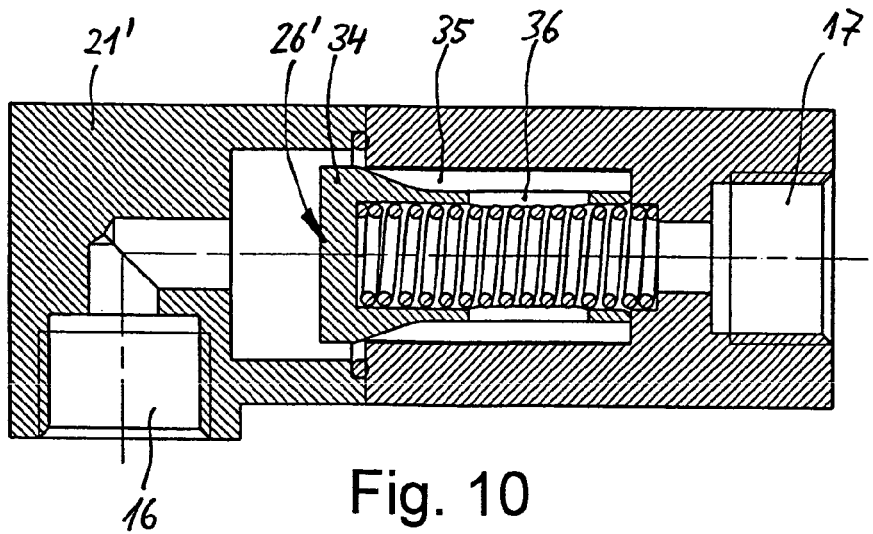
Figure 11:
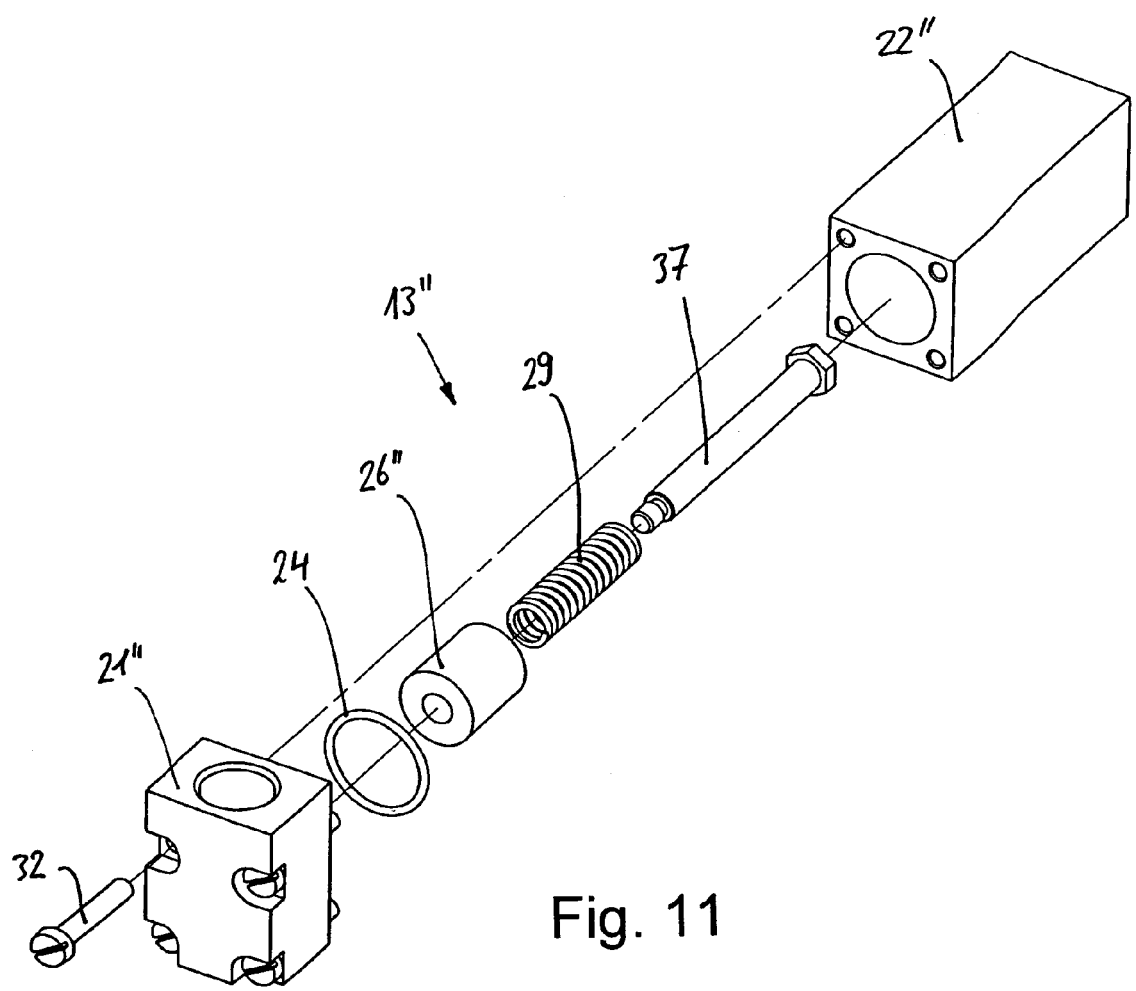
Figure 12:
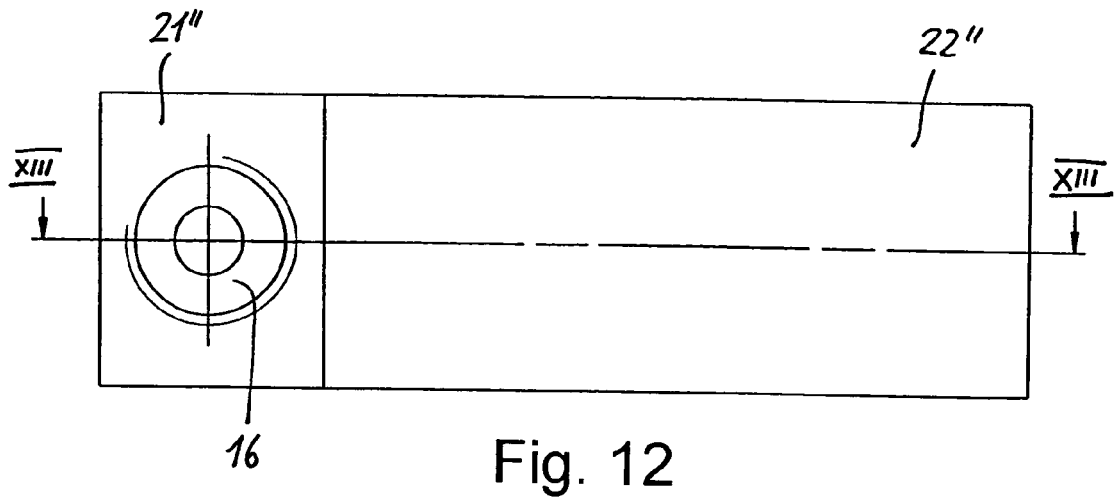
Figure 13:
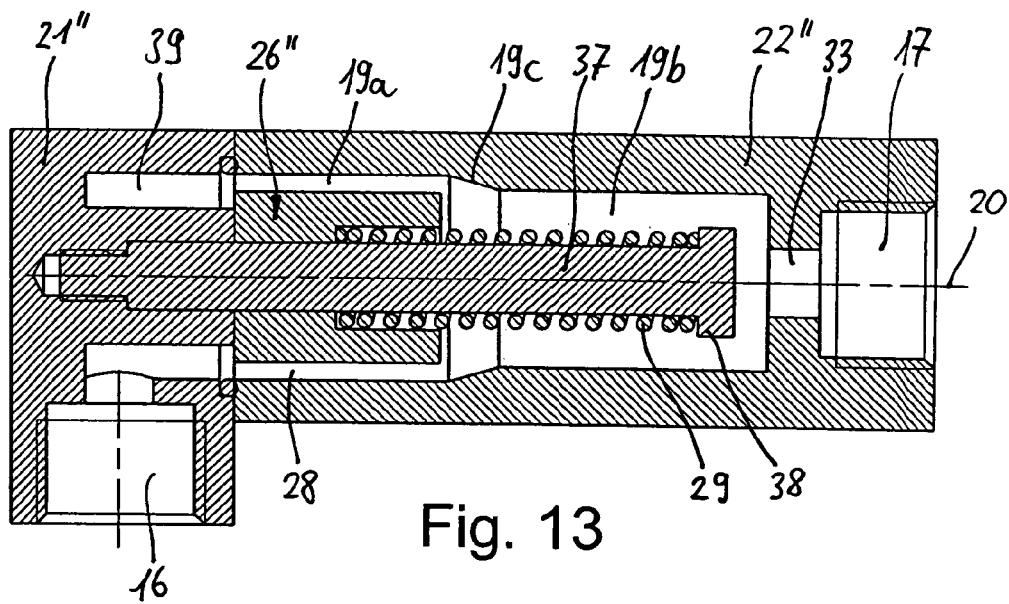
Figure 14:
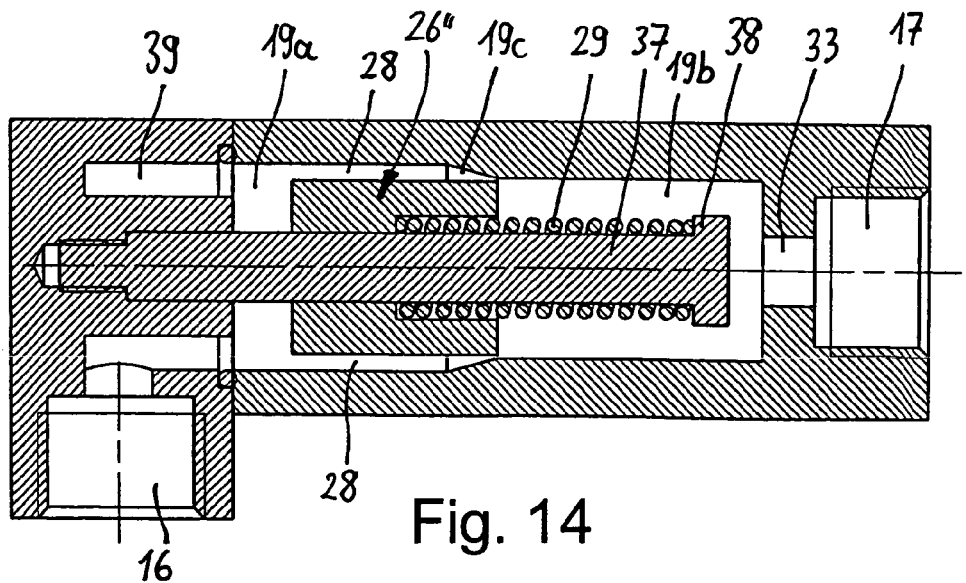

FIG. 1 shows a schematic of a cold test device as claimed in the invention,

FIG. 2 shows an exploded view of a first embodiment of the volumetric flow regulator as claimed in the invention, FIG. 3 shows a side view of the volumetric flow regulator from FIG. 2, FIG. 4 shows a section along the line IV-IV from FIG. 3, the throttle slide valve being in the forward position, FIG. 5 shows a vertical section through the volumetric flow regulator of FIGS. 2 and 3, the position of the throttle slide valve corresponding to that from FIG. 4, FIG. 6 shows a representation according to FIG. 4, the throttle slide valve being in the rear position, FIG. 7 shows an exploded view of a second embodiment of the volumetric flow regulator as claimed in the invention, FIG. 8 shows a side view of the volumetric flow regulator from FIG. 7, FIG. 9 shows a section along the line IX-IX from FIG. 8, the throttle slide valve being in the forward position, FIG. 10 shows a sectional view according to FIG. 9, the throttle slide valve being in the rear position, FIG. 11 shows an exploded view of a third embodiment of the volumetric flow regulator as claimed in the invention, FIG. 12 shows a side view of the volumetric flow regulator from FIG. 11, FIG. 13 shows a sectional view along the line XIII-XIII from FIG. 12, the throttle slide valve being in the forward position, and FIG. 14 shows a sectional view according to FIG. 13, the throttle slide valve being in the rear position.

The cold test device shown in FIG. 1 can be installed for example in automatic handling devices for electronic components, so-called handlers, and has a cold chamber 1 which is tightly surrounded by a housing 2. An electronic component 3 can be inserted into the cold chamber 1 via locks which are not shown and can be brought into contact with electrical contacts 4 such that the electrical properties of the component 3 can be measured when the component 3 is exposed to low temperatures of for example −60° C.

As is further apparent from FIG. 1, the cold test device furthermore has a cryogenic fluid supply line 5 for supplying liquid cryogenic fluid in the form of liquid nitrogen, which is routed into the interior of the cold chamber 1. Outside the housing 2 there can optionally be a pressure regulator 6 in the cryogenic fluid supply line 5 in order to adjust the liquid cryogenic fluid at high supply pressures down to the desired pressure range of for example a maximum 5 bar, if this should be necessary.

The cryogenic fluid supply line 5 within the cold chamber 1 passes into a meandering line area 7 which together with assigned evaporator heating 8 forms an evaporator 9. In the evaporator 9 liquid nitrogen is heated to above the boiling point (−195.8° C.) and thus converted into the gaseous phase. Uniform and effective heating is achieved via a fan 10 by which air is blown over the evaporator heating 8 onto the meandering line area 7.

The gaseous nitrogen is routed on from the meandering line area 7 via the cryogenic fluid line 11 to the electronic component 3. The end 12 of the cryogenic fluid line 11 is made and arranged such that the gaseous nitrogen is blown uniformly onto the body of the electronic component 3 and is uniformly cooled in the desired manner.

In the cryogenic fluid line 11 there are a volumetric flow regulator 13, 13', 13" which is detailed below for stabilizing the pressure and volumetric flow of the gaseous nitrogen, and a heating means 14 with which the temperature of the gaseous nitrogen at the end 12 of the cryogenic fluid line can be controlled and set to the desired value. For this reason on the end 12 of the cryogenic fluid line 11 there is a temperature sensor which is not detailed and which acts on the heating means 14 via a corresponding control means which is not detailed either. For example, the heating means 14 is triggered such that the temperature of the emerging gas is −60° C.

As already stated, stabilization of the gaseous volumetric flow in the cryogenic fluid line 11 takes place by the volumetric flow regulator 13, 13', 13" which is located between the meandering line area 7 and the heating means 14. A first embodiment of the volumetric flow regulator 13 is detailed below using the FIGS. 2 to 6.

The volumetric flow regulator 13 has a housing 15 with a cryogenic fluid inlet 16 and a cryogenic fluid outlet 17. The holes of the cryogenic fluid inlet 16 and cryogenic fluid outlet 17 each have a threaded connection with an internal thread 18 for connection of the cryogenic fluid line 11.

As shown by FIGS. 4 to 11, the cryogenic fluid inlet 16 discharges into a spool chamber 19 which extends centrally to the lengthwise center axis 20 within the housing 15.

The housing 15 consists of a front housing section 21 and a rear housing section 22 which can be screwed to the front housing section 21 by means of screws 32. The spool chamber 19 in the embodiment shown in FIGS. 2 to 6 is located within the front housing section 21 and is formed by a cylindrical lengthwise hole which is made in the front housing section 21 from the back end wall of the front housing section 21. To the rear the spool chamber 19 is closed by the rear housing section 22 which is attached to the back end wall of the front housing section 21 and is radially centered by means of a short centering projection 23 which projects slightly into the spool chamber 19. Sealing between the front housing section 21 and the rear housing section 22 takes place by means of an O-ring 24.

The rear housing section 22 on its front face bears a guide pipe 25 which is located centrally to the lengthwise center axis 20 and extends forward with a radial distance to the wall of the spool chamber 19 into it. A sleeve-like throttle slide valve 26 is slipped onto the guide pipe 25 and can thus be moved lengthwise on the guide pipe 25. The lengthwise through hole of the guide pipe 25 in its back end area discharges into the cryogenic fluid outlet 17. Furthermore, in the wall of the guide pipe 25 there are two opposing through openings 27 in the form of lengthwise slots, these through openings 27 being located on the back end of the guide pipe 25, i.e. adjacent to the transition region between the front housing section 21 and the rear housing section 22. The through openings 27 are used so that the gaseous cryogenic fluid which is flowing to the rear via the cryogenic fluid inlet 16 into the spool chamber 19 and from the front end of the spool chamber 19 via the annular gap 28 between the throttle slide valve 26 and the wall of the front housing section 21 can flow into the interior of the guide pipe 25 and from there to the cryogenic fluid outlet 17. The number, size and arrangement of the through openings 27 are variable and can be provided depending on need.

As follows from a comparison of FIGS. 4 and 5 on the one hand and FIG. 6 on the other, the through openings 27, depending on the position of the throttle slide valve 26, are overlapped by it to a greater or smaller distance. If the throttle slide valve 26 is in its forward position which is shown in FIGS. 4 and 5, the back end of the throttle slide valve 26 is located upstream of the through openings 27, i.e. the through openings 27 are completely opened. The throttle slide valve 26 is pretensioned by a spring 29 into this forward position; the spring is located within the guide pipe 25 and is supported with its back end on a shoulder 40 of the guide pipe 25 which projects inward. This shoulder 30 is located upstream of the through openings 27. To the front the spring 29 reaches beyond the guide pipe 25 and on its front end is supported on the inside of the closed end wall 31 of the throttle slide valve 26.

This arrangement results in that the throttle slide valve 26 is pushed increasingly to the rear, i.e. to the right, by the gas flowing into the spool chamber 19 with increasing pressure against the pretensioning force of the spring 29 and in this way increasingly closes the through openings 27, while when the gas pressure is dropping in the spool chamber 19 the slide valve 26 is pressed by the pretensioning force of the spring 29 forward again, i.e. to the left, and thus clears the through openings 27. The flow cross section of the through openings 27 and thus the volumetric flow passing through the through openings 27 thus behave inversely proportionally to the pressure of the gas flowing in via the cryogenic fluid inlet 16. The diameter of the through opening 27, the spring constant of the spring 29 and the dimensions of the spool chamber 19 and of the throttle slide valve 26 are such that even with a variable input pressure of the gas the output pressure on the cryogenic fluid outlet 17 remains largely constant.

FIGS. 7 to 10 show a second embodiment of a volumetric flow regulator 13'. The housing 15' in this embodiment in turn consists of a front housing section 21' and a rear housing section 22' which are joined to one another by means of screws 32 (FIG. 7) and are sealed by means of an O-ring 24 on their end contact surface.

The front housing section 21' is made similarly to that of the first embodiment, but extends in the axial direction much less to the rear. The wall of the front housing section 21' surrounds a front, first chamber section 19*a*. The rear housing section 22' has a cylindrical axial hole which extends from its front end concentrically to the lengthwise center axis 20 to the rear and forms a rear, second chamber section 19*b*. The diameter of the second chamber section 19*b* is less than that of the first chamber section 19*a*. Furthermore, the second chamber section 19*b* is connected via an axial connecting hole 33 to the cryogenic fluid outlet 17.

In the second chamber section 19*b* a throttle slide valve 26' is movably supported which, as in the case of the first embodiment, has the shape of a cylindrical sleeve and has a closed, front end wall 31'. The diameter of the second chamber section 19*b* thus corresponds essentially to that of the outside diameter of the throttle slide valve 26', while the diameter of the first chamber section 19a is greater than the outside diameter of the throttle slide valve 26' so that the gaseous nitrogen can flow from the cryogenic fluid inlet 16 into the annular gap 28 between the throttle slide valve 26' and the wall of the front housing section 21'.

The throttle slide valve 26' furthermore has a front slide valve section 34 with a continuously peripheral outside diameter and a following valve section with two opposite lengthwise grooves 35 which are provided on its outside surface and which extend as far as the back end of the throttle slide valve 26', but not to its front end. The number and arrangement of lengthwise grooves 35 can vary. Furthermore, in the wall of the throttle slide valve 26' in the area of the lengthwise grooves 35 there is one passage opening 36, by which a fluid connection can be established between the space of the lengthwise grooves 35 and the interior of the throttle slide valve 26'. The bottom of the lengthwise grooves 35, proceeding from the front slide valve section 34, declines gradually to the rear and thus forms a gentle transition to the lower area of the lengthwise grooves 35.

The throttle slide valve 26' is in turn pretensioned forward by the spring 29, i.e. to the left in the figures, as is shown in FIG. 9. The spring 29 is supported with its front end on the inside of the front end wall 31 of the throttle slide valve 26' and on its back end on a shoulder 30' of the rear housing section 22', which shoulder projects radially to the inside.

If the pressure of the gaseous nitrogen in the area of the cryogenic fluid inlet 16 is relatively low, the throttle slide valve 26' is pressed relatively far forward as a result of the pretensioning force of the spring 29, as is shown in FIG. 9. The front slide valve 34 in this state is located relatively far in front of the front end wall of the rear housing section 22' so that a relatively large passage for the gaseous nitrogen from the annular gap 28 to the lengthwise grooves 35 is formed. From the lengthwise grooves 35 the gaseous nitrogen can flow both via the passage openings 36 into the interior of the throttle slide valve 26' and from there to the cryogenic fluid outlet 17 and also directly via the free back end of the lengthwise grooves 35 to the cryogenic fluid outlet 17.

If the pressure of the gaseous nitrogen rises in the area of the cryogenic fluid inlet 16, the throttle slide valve 26' is pressed increasingly to the rear, i.e. to the right, so that the flow passage from the annular gap 28 into the lengthwise grooves 35 is increasingly reduced. The end position in which the throttle slide valve 26' is located entirely to the rear is shown in FIG. 10. In this state the front slide valve section 34 directly borders the front face of the rear housing section 22' so that the passage to the lengthwise grooves 35 is completely closed so that no volumetric flow or no noticeable volumetric flow can flow to the cryogenic fluid outlet 17. The open groove cross section is thus determined by how far the throttle slide valve 26' projects into the first chamber section 19a.

FIGS. 11 to 14 show another embodiment of a volumetric flow regulator 13" in which both the front chamber section 19a and also the rear chamber section 19b are located in the rear housing section 22". The front chamber section 19a in turn has a greater diameter than the rear chamber section 19b and is connected to it via a conically running transition area 19b.

The throttle slide valve 26" is made cylindrical with a constant outside diameter. The outside diameter of the throttle slide valve 26" is such that no volumetric flow or only very little volumetric flow of the gaseous nitrogen can flow from the annular gap 28 of the front chamber section 19a into the rear chamber section 19b when the throttle slide valve 26" is pressed by the inflowing gas entirely to the rear, i.e. to the right, as is shown in FIG. 14. The throttle slide valve 26" can have an outside diameter which is slightly smaller than the diameter of the rear chamber section 19b so that the throttle slide valve 26" can enter the rear chamber section 19b with little play. But it is also possible to make the outside diameter of the throttle slide valve 26" the same or larger than the diameter of the rear chamber section 19b so that the rear outer edge of the throttle slide valve 26" touches the transition area 19c and thus blocks the passage.

The throttle slide valve 26" is movably guided on a guide rod 37 which is attached in the front housing section 21" and extends from there centrally to the lengthwise center axis 20 to almost the end of the rear chamber section 19b. The guide rod 37 penetrates the axial lengthwise hole of the throttle slide valve 26" which in the rear area of the throttle slide valve 26" has a somewhat larger diameter so that the spring 29 which in this embodiment surrounds the guide rod 37 can be inserted somewhat into the interior of the throttle slide valve 26" and is supported there with its front end. The back end of the spring 29 is supported on a radial projection 38 on the back end of the guide rod 37. The throttle slide valve 26" is pretensioned forward, i.e. to the left, due to this arrangement so that at a low gas pressure in the area of the cryogenic fluid inlet 16 it adjoins the front housing section 21". In this state which is shown in FIG. 13, the gas can flow from an annular inflow chamber 39, which is provided in the front housing section 21" and which is fluid-connected to the cryogenic fluid inlet 16, to the annular gap 28 of the front housing section 19a with maximum flow rate to the rear housing section 19b and from there to the cryogenic fluid outlet 17. If the pressure rises in the area of the cryogenic fluid inlet 16, the throttle slide valve 26" is pressed increasingly to the rear and thus the passage in the area of the transition area 19c is increasingly diminished so that the volumetric flow and the pressure in the area of the cryogenic fluid outlet 17 decrease.

It is common to all embodiments that the throttle slide valve 26, 26', 26" is moved against the pretensioning force of a spring when the pressure fluctuates in the area of the cryogenic fluid inlet 16 such that the volumetric flow and the pressure in the area of the cryogenic fluid outlet 17 are made uniform.

The invention claimed is:

1. Cold test device for electronic components, with a cryogenic fluid supply line for supply of a liquid cryogenic fluid, an evaporator for converting the liquid cryogenic fluid into a gaseous cryogenic fluid, a cryogenic fluid line for transporting the gaseous cryogenic fluid to the electronic component in order to cool the electronic component with the gaseous cryogenic fluid, and with a heating means for adjusting the temperature of the gaseous cryogenic fluid, characterized in that in the cryogenic fluid line which transports the gaseous cryogenic fluid there is a volumetric flow regulator which stabilizes the pressure and the volumetric flow of the cryogenic fluid, wherein the volumetric flow regulator is arranged between the evaporator and the heating means.

2. Cold test device as claimed in claim 1, wherein the volumetric flow regulator has a housing with a cryogenic fluid inlet, a cryogenic fluid outlet and a spool chamber which is located between the cryogenic fluid inlet and cryogenic fluid outlet and in which a throttle slide valve can be moved by means of the inflowing gaseous cryogenic fluid against a pretensioning force of a spring, by which the volumetric flow flowing through the volumetric flow regulator can be varied.

3. Cold test device as claimed in claim 2, wherein the throttle slide valve comprises a slide valve sleeve which is movably located on the guide pipe which projects in the spool chamber with a radial distance to the wall of the spool chamber and which is securely connected to the housing.

4. Cold test device as claimed in claim 3, wherein the interior of the guide pipe is fluid-connected to the cryogenic fluid outlet, in the wall of the guide pipe there being at least one through opening which is overlapped to a greater or smaller distance by the throttle slide valve depending on its position.

5. Cold test device as claimed in claim 3, wherein the spring is located within the guide pipe and is supported with its front end on the inside of the end wall of the throttle slide valve.

6. Cold test device as claimed in claim 2, wherein the spool chamber has a first chamber section with a larger chamber diameter which is fluid-connected to the cryogenic fluid outlet, and a second chamber section with a smaller chamber diameter which is fluid-connected to the cryogenic fluid outlet, and wherein the throttle slide valve comprises a slide valve sleeve which determines, by its relative position to the second chamber section, the volumetric flow of the cryogenic fluid from the first into the second chamber section.

7. Cold test device as claimed in claim 6, wherein the throttle slide valve is inserted with the capacity to move into the second chamber section with narrow play and has a front valve section with a continuously peripheral outside diameter and another valve section with at least one lengthwise groove which is provided on its outside surface and which is fluid-connected to the cryogenic fluid outlet.

8. Cold test device as claimed in claim 7, wherein the lengthwise groove deepens and/or widens to the rear so that the open groove cross section is determined by how far the throttle slide valve projects into the first chamber section.

9. Cold test device as claimed in claim 7, wherein the throttle slide valve is open to the rear, wherein the spring is supported on the back end on the housing and projects forward into the throttle slide valve, and wherein the lengthwise groove is fluid-connected to the interior of the throttle slide valve via a passage opening in the wall of the throttle slide valve.

10. Cold test device as claimed in claim 6, wherein the throttle slide valve between the first chamber section and the second chamber section has a conically running transition area, and wherein the throttle slide valve at least on its back end has an outside diameter which is only slightly smaller, the same size, or larger than the inside diameter of the second chamber section, and wherein the length of the throttle slide valve is shorter than the length of the first chamber section, so that the throttle slide valve can be moved between a front position, in which its back end is away from the second chamber section, and a rear position in which its back end is adjacent to the second chamber section.

11. Cold test device as claimed in claim 10, wherein the throttle slide valve is movably guided on a guide rod which is anchored in the front part of the housing, extends through the throttle slide valve to the rear and on the back end has a stop for the spring which surrounds the guide rod.

12. Cold test device for electronic components, with a cryogenic fluid line for supply of a liquid cryogenic fluid, an evaporator for converting the liquid cryogenic fluid into a gaseous cryogenic fluid, the liquid cryogenic fluid having an associated temperature, pressure and volumetric flow, a cryogenic fluid line for transporting the gaseous cryogenic fluid to the electronic component in order to cool the electronic component with the gaseous cryogenic fluid, and with a heating means for adjusting the temperature of the gaseous cryogenic fluid, characterized in that in the cryogenic fluid line which transports the gaseous cryogenic fluid there is a volumetric flow regulator which stabilizes the pressure and the volumetric flow of the cryogenic fluid, further including a volumetric flow regulator disposed in the cryogenic fluid line between the heating means and an end of said cryogenic fluid line.

* * * * *